United States Patent
Leonardi et al.

(10) Patent No.: US 7,860,554 B2
(45) Date of Patent: Dec. 28, 2010

(54) VISIBLE-NEAR INFRARED SPECTROSCOPY IN BURN INJURY ASSESSMENT

(75) Inventors: Lorenzo Leonardi, Manitoba (CA); Jerl Payette, Manitoba (CA); Michael G. Sowa, Manitoba (CA); Mark Hewko, Manitoba (CA); Bernhard J. Schattka, Manitoba (CA); Henry H. Mantsch, Berlin (DE)

(73) Assignee: National Research Council of Canada, Ottawa, Ontario ( * ) Notice: Subject to any disclaimer, the term of this patent is extended or adjusted under 35 U.S.C. 154(b) by 2083 days.

(21) Appl. No.: 10/182,128

(22) PCT Filed: Jan. 26, 2001

(86) PCT No.: PCT/CA01/00090

§ 371 (c)(1),
(2), (4) Date: Jun. 9, 2003

(87) PCT Pub. No.: WO01/54580

PCT Pub. Date: Aug. 2, 2001

(65) Prior Publication Data

US 2006/0155193 A1 Jul. 13, 2006

Related U.S. Application Data

(60) Provisional application No. 60/178,322, filed on Jan. 27, 2000.

(51) Int. Cl.
*A61B 5/00* (2006.01)
(52) U.S. Cl. ............................ 600/473; 600/476; 600/328
(58) Field of Classification Search .................. 600/310, 600/315, 473, 475–476, 322–328; 702/19, 702/28, 172; 356/300, 345, 406, 436, 39–41; 250/227.23, 227.28
See application file for complete search history.

(56) References Cited

U.S. PATENT DOCUMENTS 4,170,987 A * 10/1979 Anselmo et al. ............ 600/475

(Continued)

FOREIGN PATENT DOCUMENTS

DE 4427101 2/1996

(Continued)

OTHER PUBLICATIONS

S.X. Zhao and T. Lu, "The Classification of the Depth of Burn Injury Using Hybrid Neural Network"; IEEE Conference on Engineering in Medicine & Biology Society, ISBN 7803-2475-7, vol. 1, pp. 815-816, Jul. 1997.*

(Continued)

*Primary Examiner*—Francis Jaworski
(74) *Attorney, Agent, or Firm*—Ade & Company Inc.; Michael R. Williams

(57) ABSTRACT

A non-invasive method of characterizing burn injuries using near infrared spectroscopy is described. In the method, a beam of light is emitted into the burnt tissue portion at two or more different tissue depths. The spectra are then compared using multivariate analysis to determine diagnostic regions of the spectra. This information is used to categorize the burn. In some cases, the diagnostic regions correspond to wavelengths related to the hemodynamics of the tissue portion. The spectra can also be repeated over time, thereby allowing trends and changes in the spectra to be measured. This data is in turn used to categorize the burn as either a superficial burn, partial thickness burn, deep partial burn or a full thickness burn. Once the burn has been categorized, the clinician can intervene as needed to treat the burn.

8 Claims, 9 Drawing Sheets

U.S. PATENT DOCUMENTS

| | | | |
|---|---|---|---|
| 4,693,255 A * | 9/1987 | Beall | 600/431 |
| 4,930,516 A * | 6/1990 | Alfano et al. | 600/477 |
| 5,042,494 A | 8/1991 | Alfano | |
| 5,074,306 A * | 12/1991 | Green et al. | 600/317 |
| 5,205,291 A | 4/1993 | Potter | |
| 5,369,496 A | 11/1994 | Alfano et al. | |
| 5,413,108 A | 5/1995 | Alfano | |
| 5,435,309 A * | 7/1995 | Thomas et al. | 600/310 |
| 5,687,730 A | 11/1997 | Doiron et al. | |
| 5,699,797 A | 12/1997 | Godik | |
| 5,701,902 A * | 12/1997 | Vari et al. | 600/473 |
| 5,747,789 A | 5/1998 | Godik | |
| 5,833,612 A | 11/1998 | Eckhouse et al. | |
| 5,883,708 A | 3/1999 | Jung et al. | |
| 5,920,390 A * | 7/1999 | Farahi et al. | 356/477 |
| 5,961,466 A | 10/1999 | Anbar | |
| 5,987,351 A | 11/1999 | Chance | |
| 6,008,889 A | 12/1999 | Zeng et al. | |
| 6,015,969 A * | 1/2000 | Nathel et al. | 250/227.27 |
| 6,032,070 A | 2/2000 | Flock et al. | |
| 6,058,324 A * | 5/2000 | Chance | 600/473 |
| 6,070,092 A | 5/2000 | Kazama et al. | |
| 6,324,417 B1 | 11/2001 | Cotton | |
| 6,381,488 B1 * | 4/2002 | Dickey et al. | 600/474 |
| 6,587,701 B1 * | 7/2003 | Stranc et al. | 600/310 |
| 6,640,133 B2 * | 10/2003 | Yamashita et al. | 600/476 |
| 7,142,304 B1 * | 11/2006 | Barbour et al. | 356/432 |
| 7,280,866 B1 * | 10/2007 | McIntosh et al. | 600/475 |
| 7,322,972 B2 * | 1/2008 | Viator et al. | 606/9 |
| 7,729,747 B2 * | 6/2010 | Stranc et al. | 600/473 |
| 2006/0094940 A1 * | 5/2006 | St-Jean et al. | 600/315 |

FOREIGN PATENT DOCUMENTS

| | | |
|---|---|---|
| WO | WO96/08201 | 3/1996 |
| WO | WO97/05473 | 2/1997 |

OTHER PUBLICATIONS

Chacko, S. et al., "Multi-layer imaging of human organs by measurement of laser backscattered radiation", May 1999, Medical and Biological Engineering and Computing, vol. 37, pp. 278-284.

Svaasand, L. O. et al., "Reflectance measurements of layered media with diffuse photon-density waves: a potential tool for evaluating deep burns and subcutaneous lesions", Mar. 1999, Physics in Medicine and Biology, vol. 44, pp. 801-813.

Stranc et al., "Assessment of tissue viability using near-infrared spectroscopy", 1998, British Journal of Plastic Surgery, vol. 51, pp. 210-217.

* cited by examiner

VISIBLE-NEAR INFRARED SPECTROSCOPY IN BURN INJURY ASSESSMENT

This application is the National Stage of International Application No. PCT/CA01/00090, filed Jan. 26, 2001 which claims the benefit under 35 U.S.C. 119(e) of U.S. provisional application Ser. No. 60/178,322, filed Jan. 27, 2000

FIELD OF THE INVENTION

The present invention relates generally to the field of medical devices.

BACKGROUND OF THE INVENTION

Cutaneous burns are one of the most destructive insults to the skin, causing damage, scarring and even death of the tissue. It has been reported that burns alone account for over 2 million medical procedures every year in the United States. Of these, 150,000 refer to individuals who are hospitalized and as many as 10,000 die (Bronzino, 1995, The Biomedical Engineering Handbook (CRC Press: Florida)). Despite the large number of annual burn cases, the accurate assessment of burn severity remains a problem for the burn specialist. The ability to distinguish between burns that will heal on their own versus those that will require surgical intervention is particularly challenging. Generally, the depth of a burn injury determines and is inversely related to the ability of the skin to restore and regenerate itself. Burns involve damage to the dermis in varying amounts, reducing the dermal blood supply and altering the skin hemodynamics. Highly destructive burns have only a marginal residual blood supply to the dermis that may result in ischemia and ultimately necrosis of the dermis, as the re-epithelialization of the tissue depends on the viable dermis below the burned tissue. Thermal injuries are clinically classified according to the depth of the injury as superficial (epidermal), partial thickness (epidermal and varying levels of dermal) and full thickness (epidermal and dermal). Superficial burns are mild burns whereby the tissue is capable of regenerating the epidermis. Partial thickness injuries destroy a portion of the dermal layer, although sufficient dermis usually remains for re-epithalization to occur with adequate vasculature. Deep partial and full thickness injuries involve destruction of the dermal layer and what little if any remains of the dermis is insufficient to regenerate due to a reduced dermal blood supply. Currently, the diagnosis is usually done by visual inspection and is based on the surface appearance of the wound.

As a research tool, biopsies followed by histological examination remain the gold standard for gauging burn depth (Chvapil et al, 1984, *Plast Reconstr Surg* 73: 438-441). However, the major drawback of this technique is that it provides a static picture of the injury reflecting the extend of tissue damage at the time the biopsy was taken. Since burn injuries are dynamic and change over the early postburn period, a single biopsy taken at the initial assessment of the injury may not accurately predict outcome. For this reason, biopsies are not generally relied upon in the clinical assessment of burn injuries.

Fluorescent dyes, such as indocyanine green, have also been used to assess the severity of burns. This invasive method, which is used specifically to monitor tissue perfusion, requires that a fluorescent dye be injected into the systemic circulation of a patient (Gatti et al, 1983, *J. Trauma* 23: 202-206). Following the injection of dye, vessels that are intact and have a functional blood supply will fluoresce when illuminated by the appropriate wavelength of light. The presence or absence of dye fluorescence therefore acts as an indicator of tissue perfusion. While this method has demonstrated success in distinguishing superficial from full thickness burns (i.e. presence or absence of fluorescence), it cannot easily differentiate those burn types that are between the two extremes. Furthermore, the extended washout times of the dye limit the frequency with which it can be used to assess a dynamic injury. As a result, indocyanine green has not yet met with clinical acceptance even though it has been available for burn diagnosis for over a decade. Other techniques, including thermography (Mason et al, 1981, *Burns* 7: 197-202), laser Doppler (Park et al, 1998, *Plast Reconstr Surg* 101: 1516-1523), ultrasound (Brink et al, 1986, Invest Radiol 21: 645-651) and light reflectance (Afromowitz et al, 1987, *IEEE Trans Biomed Eng* BME34: 114-127) have also been developed to assess burn injuries.

U.S. Pat. No. 5,701,902 describes the use of fluorescence excitation and simultaneous IR spectroscopy to characterize burns. Specifically, in this method, the fluorescence of elastin, collagen, NADH and FAD are analyzed, and the total amount of hemoglobin and relative amounts of oxygenated hemoglobin and reduced hemoglobin as well as the water reflectance are also determined. The data is then compared to data from similar skin types in a database which is in turn used to characterize the burn. As can be seen, this process is invasive as it requires the injection of fluorescent dyes and also relies on the use of a database for characterizing the burn injury.

U.S. Pat. No. 4,170,987 teaches a medicinal skin diagnosis method which uses a rotating mirror and three detectors (IR, red and green) onto which the same pixels of the patient's skin sampled in the line scan are simultaneously imaged. From the respective three associated stored digital values per pixel, ratio numbers are then formed which can be displayed on a color monitor as a false-color image or can be printed.

Canadian Patent Application 2,287,687 teaches a device for generating data for the diagnosis of the degree of injury to a patient's skin tissue wherein a halogen lamp is used to illuminate a skin portion. The remitted light from the skin surface is recorded by a multispectral camera and the spectral images are analyzed pixelwise using suitable software. Classification of the skin injury is carried out by specific ratio formations and comparison values of degrees of injury to known skin tissue patterns.

As discussed above, the most widely used diagnostic method for diagnosing burn injuries remains visual evaluation by an experienced physician. The prior art methods described above either provide a static picture of a burn injury or rely on databases for assistance in diagnosing burn injuries. Clearly, the need exists for a reliable, non-subjective, and easy to handle technique to evaluate burn injuries in the early post-burn period that provides diagnostic as well as prognostic information on the severity of the injury.

SUMMARY OF THE INVENTION

According to a first aspect of the invention, there is provided a method of characterizing a burn comprising: emitting a beam of near infrared light into a burnt tissue portion to a first depth; collecting and analyzing reflected light from the beam, thereby producing a first depth spectrum; emitting a beam of near infrared light into a burnt tissue portion to a second depth; collecting and analyzing reflected light from the beam, thereby producing a second depth spectrum; comparing the first depth spectrum and the second depth spectrum; and categorizing the burn based on said comparison.

According to a second aspect of the invention, there is provided a method of characterizing a burn comprising: at a first time point: (a) emitting a beam of near infrared light from into a burnt tissue portion at a first tissue depth; (b) collecting and analyzing reflected light from the beam, thereby producing an early first depth spectrum; (c) emitting a beam of near infrared light from into a burnt tissue portion at a second tissue depth; (d) collecting and analyzing reflected light from the beam, thereby producing an early second depth spectrum; at a second time point: (e) emitting a beam of near infrared light from into a burnt tissue portion at said first tissue depth; (f) collecting and analyzing reflected light from the beam, thereby producing a late first depth spectrum; (g) emitting a beam of near infrared light from into a burnt tissue portion at said second tissue depth; (h) collecting and analyzing reflected light from the beam, thereby producing a late second depth spectrum; and characterizing said burnt tissue portion based on spectral changes over time at said first and second tissue depths.

DESCRIPTION OF THE PREFERRED EMBODIMENTS

Figure 1:
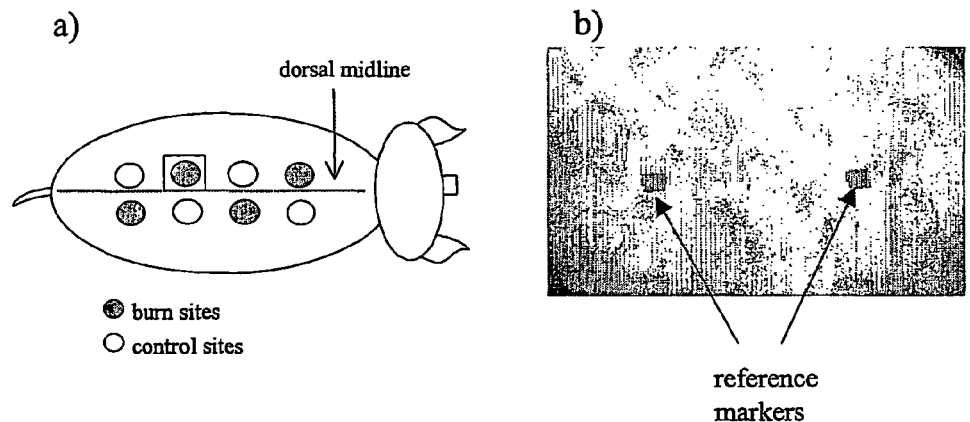
FIG. 1 shows the layout of the burn and control sites on the dorsal surface of the animal. (a) pictorial and (b) photographic representation.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As used herein, superficial burns refer to mild burns having only epidermal damage, wherein the tissue is capable of regenerating the epidermis.

As used herein, partial thickness burns refer to burns having epidermal and varying levels of dermal damage, wherein a portion of the dermal layer is destroyed but sufficient dermis may remain such that effective re-epithalization will occur with adequate vasculature.

As used herein, deep partial thickness burns refer to burns having dermal destruction to the extent that an insufficient dermal layer may exist such that regeneration of the dermis is not possible.

As used herein, full thickness burns refer to burns having dermal destruction to the extent that the dermal blood supply is so reduced that regeneration of the dermis is not possible.

As used herein, oxygen saturation refers to the relative amount of oxygenated hemoglobin to total amount of hemoglobin.

Described herein is a method of diagnosing and characterizing burn injuries wherein near infrared spectra are taken of a burnt tissue portion at two or more depths. The spectra may then be compared and analyzed using an algorithm that uses multivariate statistical analysis methods as known in the art to determine regions of high significance or diagnostic regions of the spectra. In some embodiments, these diagnostic regions correspond to spectral regions related to or that can be used to determine oxygen saturation, hemodynamics and hydration characteristics of the damaged tissue portions, as discussed below. This information allows for classification of the burn injury as described below, and allows for the appropriate steps to be taken by the clinician.

In other embodiments, spectra are taken at different depths over two or more time periods so that trends or changes in the spectra can be determined. This information can then be used to classify or categorize the burn.

In yet other embodiments, spectra are taken at two or more depths and the spectra are compared at wavelengths corresponding to oxygen saturation, hemodynamics and hydration, as discussed below.

That is, in the described method, near infrared spectroscopy is used to noninvasively distinguish between surface and subsurface molecular changes that are caused by the burn injury. Specifically, the remaining residual cutaneous blood supply at the dermis following an injury is directly related to the extent or depth of tissue damage. Increased depth of thermal injury means there is a greater portion of the vessels that are damaged and as a result the transport of blood to the tissue is impaired. Therefore, knowledge of the skin hemodynamics following an injury can define for clinicians the extent and depth of damage.

Furthermore, the oxygenated and deoxygenated forms of hemoglobin have different extinction coefficients in the near infrared region. The data is used to calculate the oxygen saturation of the tissue, as a measure of the relative amount of oxygenated hemoglobin to the total amount of hemoglobin, thereby providing a quantifiable measure of the oxygen transport in tissue. Severe burns resulting from prolonged contact with a heat source are characterized by more heat conduction in deeper tissue resulting in tissue ischemia and vascular damage. In tissue, the total hemoglobin present can be used to represent a measure of tissue perfusion or blood volume. Burns result in complex responses related to hypo- and hypervolemia, ischemia and hypoxia. These responses are discernible with near infrared spectroscopy and provide meaningful insight into the local cutaneous microcirculatory changes associated with burn injuries.

As discussed above, the extent and depth of burn injury dictates treatment. Therefore, the main clinical question lies in grading the thermal injury and assessing the extent of the viable tissue underneath the wound. The near infrared wavelength range is ideally suited for the noninvasive evaluation of tissue chromophores deep within tissue. This suitability stems from the optical properties of tissue in the near infrared region of the spectrum. Optical properties of tissue can be described by two basic processes: absorption by the tissue chromophores and scattering by tissue constituents. When light impinges on tissue, a portion is absorbed by chromophores dispersed throughout the cellular and intercellular space. The absorption of light by tissue chromophores is weak compared to the extent of scattering in the near infrared region. Tissue scattering represents the major contribution to the attenuation of near infrared light. Scattering can occur due to refractive index variations in tissue or by elastic scattering such as the interaction with collagen in tissue. A single photon entering a tissue sample will experience many scattering events as it propagates through the medium. The interaction of light with multiple scatters results in an alteration from its original direction. In tissue these multiple scattering events are highly forward directed, i.e. light propagates in a forward direction. Therefore, the majority of the light penetrates deep within tissue before being scattered out of the tissue. The measured reflectance not only provides information on the near surface absorption but also absorptions deep inside the tissue.

Figure 8:
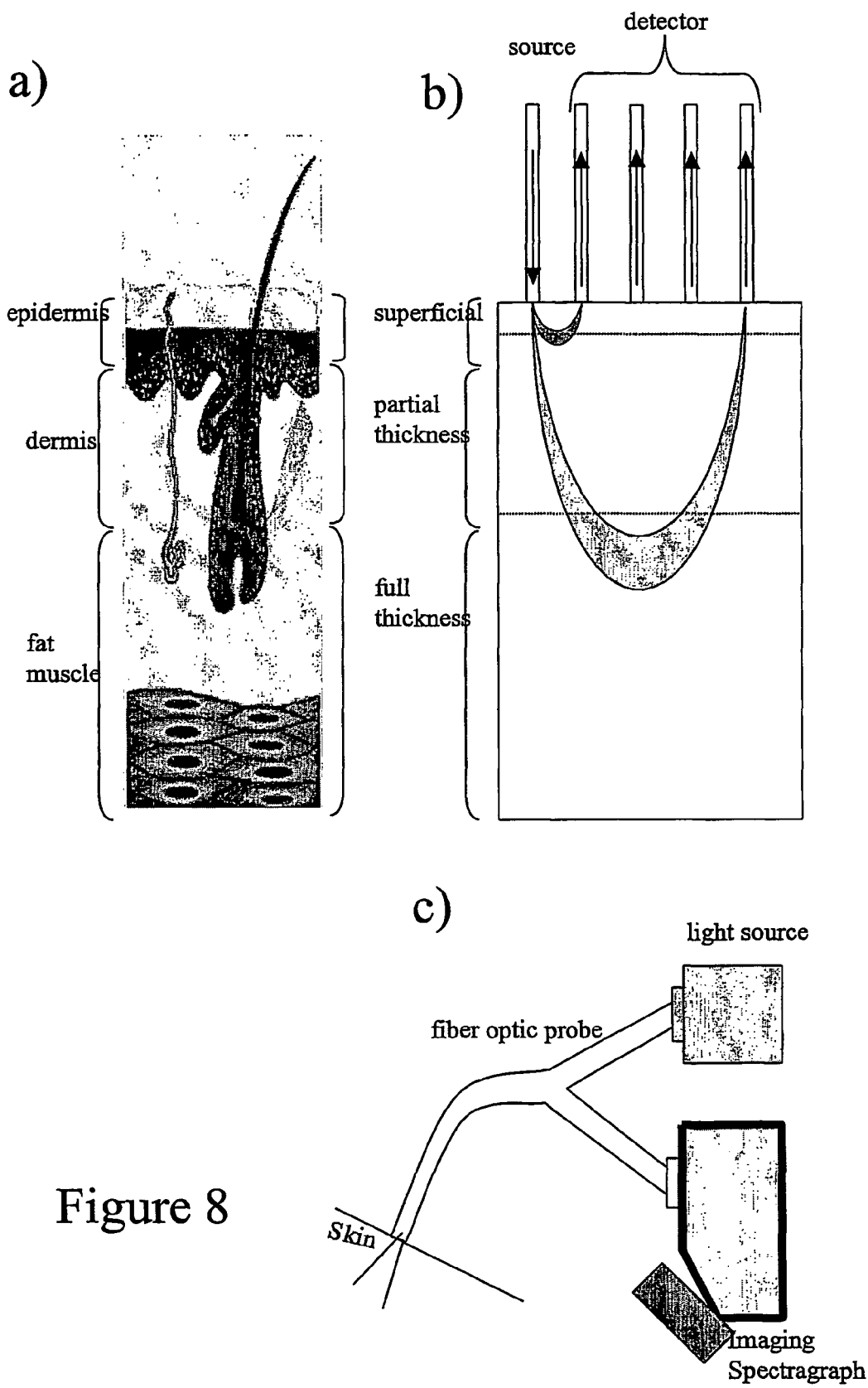
FIG. 8 is a schematic diagram of the light path through skin (left) and the penetration depth (right) at several source-detector positions.

In an optical geometry such as reflectance that involves placing a detector some finite lateral distance away from the incident light, a small fraction of the scattered light can be measured. Tissue constituents have attenuated this light from the original source by the absorption of tissue chromophores as well as from tissue scattering components. The measured attenuation is also related to the separation distance between the light source and the detector. The larger the source-detector separation the larger the attenuation since the light has undergone additional scattering to emerge out of the tissue. Therefore, the penetration depth of the observed light is dependent on the separation distance between the source and detector. The further the detector is placed from the source, the greater the depth probed into the tissue as demonstrated in FIG. 8. In order for light to reach a detector a set distance away from the source, the light must traverse a path through the media, denoted by the shaded region. As the source-detector separation increases, the path increases and the depth sampled into the medium also increases. These paths have been described by a number of authors using both Monte Carlo simulations (Long et al, 1996, *Special Publications of the Royal Society of Chemistry* 194: 176-184; Flock et al, 1989, *IEEE Trans Biomed Eng* 36: 1162-1168) and time or frequency resolved spectroscopic techniques (Hemelt et al, 1997, *Biotechnol Prog* 13: 640-649; Hemelt et al, 1999, *Biotechnol Prog* 15: 622-630; Cui et al, 1991, *Opt Lett* 16: 1632-1634). Essentially, by acquiring spectra at various source-detector separation, one can obtain spectroscopic information at different depths into the tissue.

The investigation of the epidermis as well as the deep dermis is ideal for burn depth assessment. This technique can provide depth dependent hemodynamics that are of vital importance in the assessment of tissue viability and burn depth. Near infrared spectroscopy can be applied as a noninvasive method to investigate the depth dependent circulatory alterations that arise from thermal damage to the skin. Herein, an acute porcine model to demonstrate the potential of near infrared spectroscopy to distinguish burns of varying severity. Thermal injuries disrupt the blood flow and oxygen delivery to the damaged tissue. The severe alteration of the microvascular integrity due to a thermal insult results in dramatic hemodynamic changes such as tissue ischemia and impaired tissue perfusion. These factors lead to a relative change and distribution of the levels of oxyhemoglobin and deoxyhemoglobin in tissue that can be measured by near infrared spectroscopy and used to assess the degree of thermal damage or tissue viability.

Furthermore, near infrared reflectance spectroscopy and imaging provides a non-invasive means of assessing the balance between oxygen delivery and oxygen utilization in tissue. The principal benefit of using near infrared spectroscopy and imaging is that regional variations in tissue hemodynamics can be discerned objectively. The main advantage of using near infrared light is the extended tissue sampling depth achieved. Near infrared light between 700-1100 nm can penetrate deep within tissue providing vital burn injury related information. Wound healing involves a number of different processes that must be carried out to accomplish repair. However, many of these processes are dependent on the oxygen delivery to the damaged tissue. Hemoglobin provides an endogenous marker of oxygenation. The oxygenated and deoxygenated states of hemoglobin have different extinction coefficients in the near infrared region. Therefore, contained within the near infrared absorption spectrum is the relative concentration of both the oxy- and dexoy-hemoglobin. A measure of the combined amounts of oxy- and deoxy-hemoglobin, or total hemoglobin, is related to tissue blood volume which can be used as an indicator of tissue perfusion while the ratio of oxygenated to total hemoglobin represents the oxygen saturation of tissue (Stranc et al, 1998, *Br J Plast Surg* 51: 210-217; Thomiley et al, 1997, *Adv Exp Med Biol* 411: 481493; Sowa et al, 1997, *Appl Spec* 51: 143-152).

Example I

Animal Model

Following a 10 day acclimatization period, adult Yorkshire cross swine weighing between 40 and 50 kg were premedicated with an intramuscular injection of midazolam (0.3 mg/kg), atropine (0.02 mg/kg), and ketamine (20 mg/kg). Anesthesia was then induced by mask and the pigs were intubated and mechanically ventilated. Isoflurane (1.5-2.5%), was delivered through the ventilator (via 40-60% oxygen mixed with medical air at 3.0 L/min) to maintain anesthesia for the duration of the experiment. Systemic oxygen saturation, heart rate, and blood pressure were monitored throughout the experiment. Core body temperature was maintained at 39.0° C.±0.5° C. Blood samples for blood gas and electrolyte analyses were acquired prior to thermal injury and every hour thereafter.

Following anesthesia, both sides of the dorsal midline were shaved and eight sites, each 3 cm in diameter, were marked on the back of the animal using a custom-made template. Four of the sites were located on the right side of the dorsal midline while the other four were located on the left side. Preburn spectra were then acquired at each site. Burn injuries were then created on four of the eight sites by applying a heated brass rod (100° C.) to the skin with a constant pressure (2000 g). By altering the length of time the brass rod was applied to the skin, a variety of burn injuries were created. Superficial burns were created in 3 seconds, intermediate partial thickness in 12 seconds, deep partial thickness in 20 seconds and full thickness burns in 75 seconds. The remaining four uninjured sites were used as controls. For the sham-controls, the brass rod was warmed to 39° C. (the body temperature of the pigs) and held on the animals' skin at previously defined locations with constant pressure (2000 g) for 3, 12, 20 and 75 seconds to match the times used for the burn injuries. Immediately following removal of the brass rod, control and postburn measurements were acquired. Measurement sequences were then acquired hourly until 5 sets of measurements were completed.

The animals were anesthetized for the entire experiment and closely monitored throughout. At the end of the experiment, the animals were immediately euthanized without any recovery of consciousness. All procedures were performed in accordance with the Canadian Council on Animal Care. The protocol was approved by the Animal Care Committee at the Institute for Biodiagnostics (Winnipeg, MB).

The general burn layout, depicted in FIG. 1, shows the relative positions of the burn and control sites.

Example II

Visible-Near Infrared Spectroscopy

Visible-near infrared spectra were collected with an NIR-Systems 6500 (Foss, Silver Springs, Mass.) spectrometer using a custom bifurcated fiber optic bundle (Fiberguide Industries, Stirling, N.J.). The multifiber probe consisted of five optical fibers, one to illuminate the tissue and four to collected the remitted light. The illumination and collection fibers were 2 m in length with a core diameter of 600 and 200 µm, respectively. The fiber order at the head of the probe were placed in a co-linear arrangement beginning with the illumination and subsequent collection fibers spaced 1.5 mm from each other. Therefore, the distance of the four collection fiber from the illumination source were 1.5, 3, 4.5, and 6 mm. The illumination optical fiber was coupled to a 100 W quartz tungsten halogen white light source (Oriel, Strattford, Conn.). The four collection optical fibers were placed at the entrance of an imaging spectragraph (Sciencetech Inc., London, On, Canada) covering the 500 to 1100 nm range. A back thinned illuminated 1024×128 pixel area image CCD detector (Hamamatsu, Bridgewater, N.J.) cooled to −10° C. was used as the detection element in the spectragraph. Each image, containing the spectrum from all of the four input fibers, consisted of five co-added images, which were parsed and binned into four separate raw reflectance spectrum. A 99% Spectralono reflectance standard (LabSphere Inc., North Sutton, N.H.) was used as a reference to convert raw data into reflectance spectra. Each reflectance spectrum consisted of two 32 co-added scans collected between 400-2500 nm at 10 nm resolution.

Near Infrared Imaging

Near infrared reflectance images of 256×256 pixels were collected between 650-1050 nm at 10 nm increments using a Photometrics Series 200 CCD camera (Photometrics, Tucson, Ariz.) fitted with a Nikon Macro AF60 lens and a 7 nm bandpass (FWHH) Lyot type liquid crystal tunable filter (LCTF) (Cambridge Research Instruments, Cambridge, Mass.). Each image was acquired with a 200-msec exposure time. The white-side of a Kodak Gray Card (Rochester, N.Y.); was used as a reference.

Near Infrared Depth Spectroscopy

Near infrared spectra were collected with an imaging spectragraph using a multifiber optic bundle (Fiberguide Industries, Stirling, N.J.). The multifiber probe consisted of five optical fibers, one to illuminate the tissue and four to collect the re-emitted light. The distance of the four collection fibers from the illumination source were 1.5, 3, 4.5, and 6 mm. The illumination optical fiber was coupled to a 100 W quartz tungsten halogen white light source model 77501 (Oriel, Strattford, Conn.). The four collection optical fibers were placed at the entrance of the imaging spectragraph (Sciencetech Inc., London, On, Canada) covering the 500 to 1100 nm range. A back thinned illuminated 1024×128 pixel area image CCD detector model C7041 (Hamamatsu, Bridgewater, N.J.) cooled to −10° C. was used as the detection element in the spectrograph. Each image, containing the spectrum from all of the four input fibers, which were parsed and binned into four separate raw reflectance spectra. A 99% Spectralon® reflectance standard (LabSphere Inc., North Sutton, N.H.) was used as a reference to convert raw data into reflectance spectra. The measured attenuation is related to the separation distance between the light source and the four detection or collection fibers. The penetration depth of the observed light is dependent on the separation distance between the source and the collector. The further the collector is placed from the source, the greater the depth probed into the tissue.

Example III

Data Processing

The multiplicative scatter correction (MSC) method was used to reduce the multiplicative and additive scatter effects that occur between a series of spectra. For every animal, an average spectrum was calculated for the time series of spectra that were taken from each burn type. Individual spectra of the series were assumed to deviate in both an additive (a) and multiplicative (m) fashion from the average spectrum.

$$x^*_{ik} = a + mx_k \quad (1a)$$

The scatter contribution in the individual spectra is given by $x^*_{ik}$. The multiplicative and additive coefficients were determined by linear least squares estimates of the mean spectra over the different wavelengths for each burn. Corrected spectra were obtained by subtracting the additive and dividing by the multiplicative terms of the least squares fit.

$$X_{ik,new} = (x_{ik} - a)/m \quad (2a)$$

The MSC method was used to preprocess all data prior to implementing a parallel factor analysis (PARAFAC).

Example III

Multivariate Data Processing

A time series of near infrared spectra were collected from selected sites on the dorsa of 5 animals. The first time point in the series was acquired prior to thermal injury. Subsequent points in the time series were acquired at fixed time intervals after the injury. The experimental design results in a rich set of data consisting of many variables (reflectance response over the 400-2500 nm wavelength range) observed on several occasions. (longitudinal measurements) and measured at several sites or groups (cross-sectional data) over a sample population of 5 animals. Parallel factor analysis is used to try to isolate and recover the spatial, spectral and temporal changes in reflectance of the skin due to the varying degree of thermal insult.

Parallel factor analysis is used to explore the time series of spectral data by identifying the "pure" molecular species that contribute to the spectra and determining how these "pure" species are affected by thermal insults of varying magnitude. The temporal variation of these species following the insult was also explored using the same method. Identifying the components in an unknown sample is one of the oldest problems in chemistry. The identification of the species that contribute to the response in a highly convolved series of spectra is particularly challenging when little or no information is available on the nature and relative concentrations of the constituents that make up the system. In such situations, exploratory factor analysis techniques can be applied.

Two-way factor analysis approaches attempt to provide an interpretable model of the data by imposing physically meaningful constraints in the decomposition of the data. Generally, this is accomplished by rotating (performing a linear transformation) a truncated set of the latent components (often starting from the principal components) of the data subject to a set of physically meaningful constraints. The resulting factors are intended to retrieve the individual underlying "pure" components of the measured multicomponent system. Such approaches, which are usually referred to as self-modelling curve resolution methods, often suffer from rotational ambiguity when applied to spectroscopic data. In these instances the number of constraints are too few to provide a unique rotation or solution and therefore a number of possible factor models can exist. Parallel factor analysis is an N-way decomposition model originating from Psychometrics (Harshman and Lundy, 1984, in *Research Methods for Multimode Data Analysis*, Law et al eds (New York: Praeger); Burdick, 1995, *Chem Intell Lab Sys* 28: 229-237) which is aimed at overcoming the rotational problem encountered by two-way methods. In the experimental design, dorsal sites with varying degrees of thermal injury were monitored spectroscopically over time. The data has an intrinsic three-way structure consisting of the three fixed variables: degree of thermal injury, observation time and the wavelengths at which the reflectance of the skin was monitored. PARAFAC can exploit this structure while imposing further constraints in order to resolve the problem of rotational ambiguity. In spectroscopic applications, a nonnegativity constraint is usually invoked. This constraint ensures that the derived "pure" factors have a positive or zero contribution at each time point, thereby avoiding negative constituent concentrations. The nonnegativity constraint also ensures that there are no spectral regions of negative optical density for the derived "pure" components. These constraints provide rotational solutions that lead to physically meaningful factors and potentially, to the pure components that make up the system.

For clarity, a brief description of the mathematical nomenclature used to describe the variables will be presented. In tensor notation, a scalar ($0^{th}$ order tensor) is indicated by lower-case italics, a vector ($1^{st}$ order tensor) by a bold lower-case letter, two-dimensional matrices ($2^{nd}$ order tensor) by bold capital letters, and underlined bold capitals for three-dimensional matrices ($3^{d}$ order tensor). The capital letters I, J, K, L and M are used to indicate the dimensionality of the various tensors. Therefore, the $ij^{th}$ element of a matrix X is designated as $x_{ij}$ and the $ijk^{th}$ element of a matrix Y as $y_{ijk}$.

Figure 2:
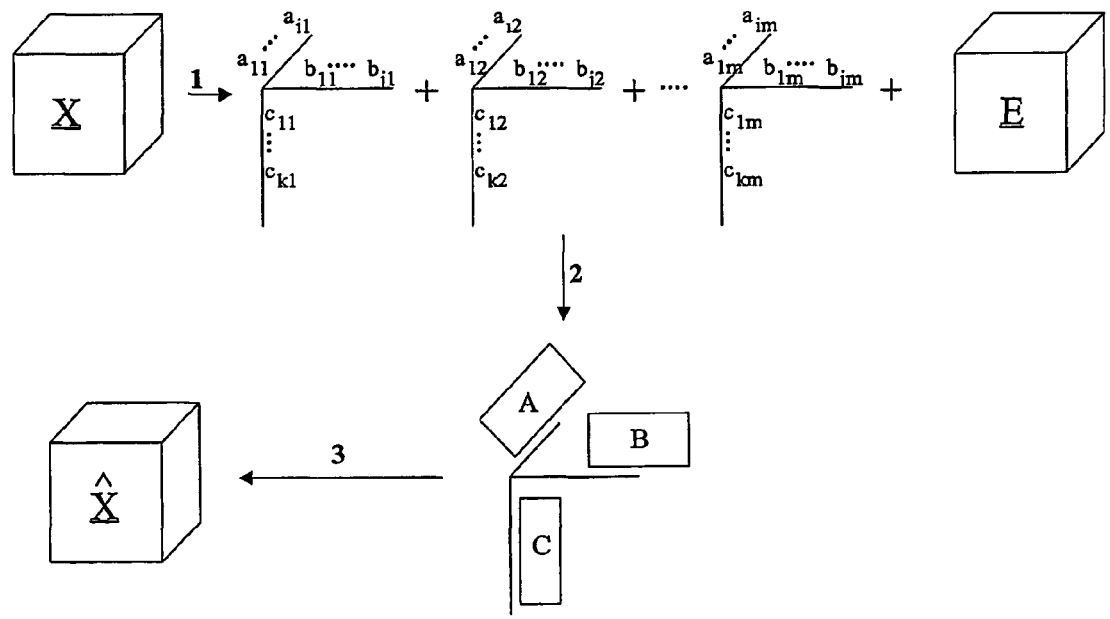
FIG. 2 is a descriptive diagram of the three-way decomposition of matrix X into factors A, B, and C.

Although PARAFAC is an N-way decomposition method, its application to burn injury evaluation is three-way involving time, burn, and spectral absorbance. A triad of loading matrices represents the PARAFAC model of the three-way data set.

$$x_{ijk} = \sum_{m=1}^{M} a_{im} b_{jm} c_{km} + e_{ijk} \tag{2}$$

where $a_{im}$, $b_{jm}$, and $c_{km}$ are the loading elements of the decomposed data set consisting of M factors and E the data residual matrix. M represents the number of underlying factors or components in the data. In the two-way factor analysis there is rotational ambiguity that leads to a continuum of factors satisfying the factor model. However, the three-way decomposition described in both equation 2 and FIG. 2 represent the "pure" components contained within the data with respect to the a, b, and c factors. In the case of spectral data, the "pure" spectrum of each of the components contained within the data will be expressed as one of the matrices containing M spectra. Two-way decomposition methods produce one score and one loading matrix. The loadings are orthogonal projections of the latent variables in the data with scores representing the scalar weightings of each of the variables. The three-way PARAFAC decomposition produces one score and two loading matrices. Another common notation for both equation 2 and FIG. 2 was the Kronecker tensor product ⊗ to describe the model (Burdick, 1995).

$$\underline{X} = \sum_{m=1}^{M} a_m \otimes b_m \otimes c_m \tag{3}$$

The decomposition produces three matrices related to 1) the spectroscopic changes 2) the variation with degree of thermal injuries and 3) the time course of the changes. Multiway data analysis provides a means to investigate and compare the spectroscopic time-courses of the various burns. Therefore, the spectral variations in the (temporal) response to the burn can be effectively isolated from the static independent components.

The factors in the PARAFAC analysis are determined using an iterative alternating least squares method. The convergence criterion used in the PARAFAC analysis to terminate the iterative procedure utilizes the relative difference in the fit between two consecutive iterations. The interactive procedure terminates when this difference is below a value of $10^{-6}$. A constraint of nonnegativity was also placed on the wavelength factors of the PARAFAC analysis to ensure that the extracted wavelength factors or "pure" components have no region of negative optical density. This method requires an initial guess or starting value to determine the underlying factors or solution. To avoid a solution whereby a local minimum is reached, a random set of starting values are used for each run. The PARAFAC analysis is run twice using a random set of starting values for each run. A consistent set of solutions for each run helps ensure that the global solution is obtained. If essentially the same factors are obtained in each run, there is little probability that a local minimum was reached and the solution is unique. The PARAFAC analysis was run twice and the results compared to ensure that the global minimum was reached.

Burn Injury Assessment

As discussed above, thermal injuries disrupt the blood flow and oxygen delivery to the damaged tissue. The severe alteration of the microvascular integrity due to a thermal insult results in dramatic hemodynamic changes such as tissue ischemia and impaired tissue perfusion. These factors lead to a relative change and distribution of the levels of oxy- and deoxy-hemoglobin in tissue. These changes can be measured by near infrared spectroscopy and used to assess the degree of thermal damage or tissue viability. The relative oxygen saturation ($S_tO_2$), a measure of the relative amount of oxygenated hemoglobin to the total amount of hemoglobin present (defined as $S_tO_2=[HbO2]/([HbO2]+[Hb])$), provides a quantifiable measure of the oxygen transport in tissue. The combined measure of oxy- and deoxy-hemoglobin, or total hemoglobin ([tHb]), is related to tissue blood volume which can be used as an indicator of tissue perfusion. The oxygenated and deoxygenated forms of hemoglobin have different extinction coefficients across the near infrared region. Using two or more of the extinction coefficients for oxy- and deoxy-hemoglobin, the $S_tO_2$ and [tHb] for tissue can be determined from a near infrared spectrum of tissue. Hemoglobin concentrations per unit photon pathlength were determined by fitting the absorption coefficients of the oxy- and deoxy-hemoglobin to the observed reflectance attenuation expressed in optical density units over the spectral range of 740-840 nm. The underlying water absorption bands at 730 and 830 nm were subtracted from the spectrum prior to fitting the reflectance attenuation. Oxygen saturation and/or total hemoglobin can be determined from the near infrared images and depth dependent spectroscopic measurements. Each method provides a particular description of the hemodynamic changes occurring with the injury.

Spectroscopic Images

Figure 6:
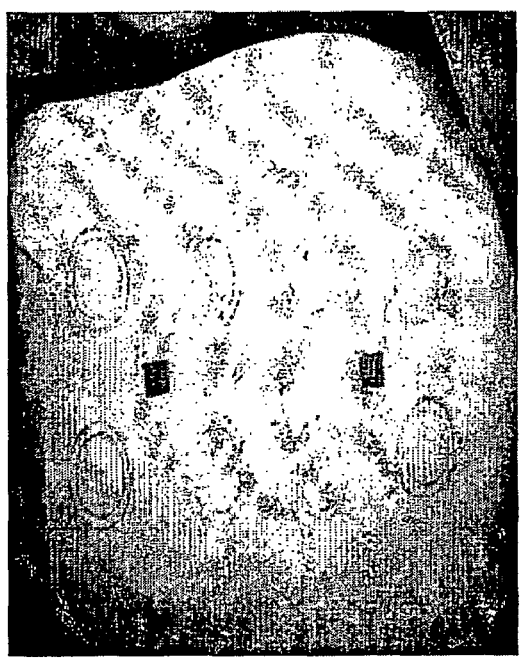
FIG. 6 shows the pre-burn (left panels) and post-burn (right panels) injuries. The upper panel is a visual (photographic) representation of deep partial thickness (a), superficial (b), full thickness (c) and intermediate partial thickness (d) burns. The lower panels are the corresponding near infrared oxygen saturation images.
Figure 6:
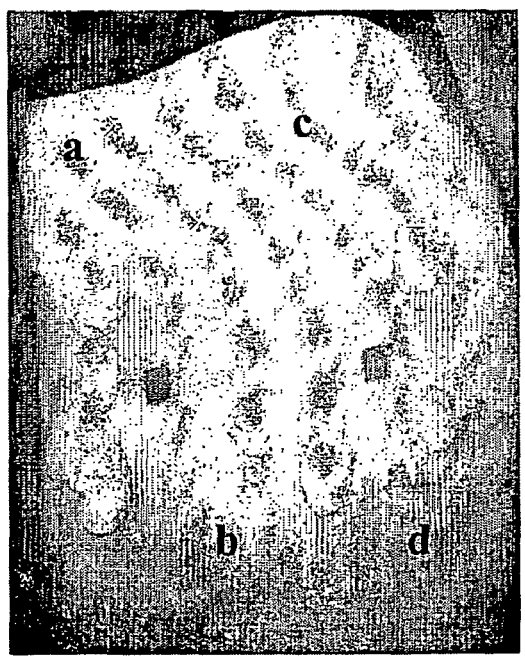
Figure 6:
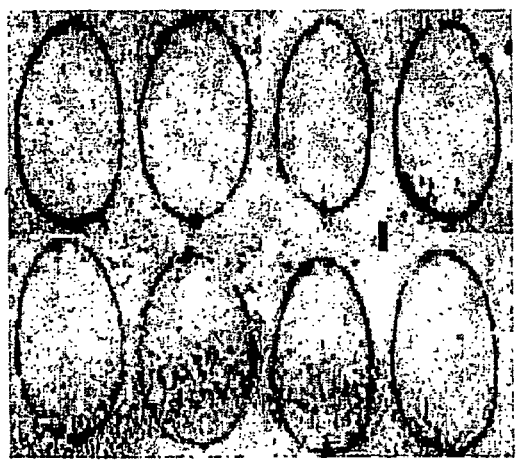
Figure 6:
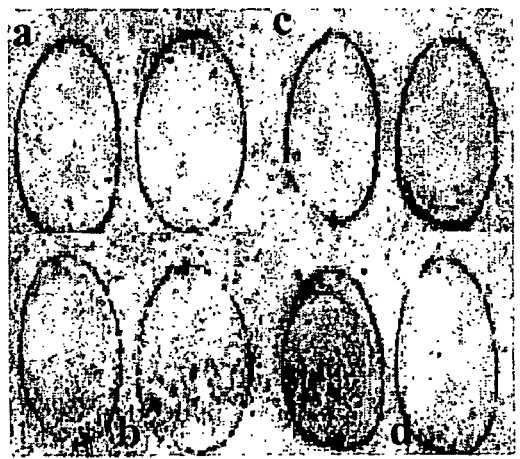

Photographs of the pre- and post-burn injuries are reproduced in the upper panels of FIG. 6. A visual inspection of the wound clearly identifies the superficial burn (FIG. 6, site b) from the more extensive and severe burns. Assessment of the partial and full thickness injuries is difficult and subjective with visual observation in the early post burn period. Tissue oxygen saturation images of the dorsal region of the pig provides a visual survey of tissue oxygenation. The lower panels of FIG. 6 show tissue oxygen saturation images of both the control and burn injures before and 4 h after the initial insult. The control sites and surrounding non-involved tissue appear bright which indicates normal tissue oxygen saturation. However, the injured sites display a drop in oxygenation following the thermal insult. Sites with low tissue oxygenation appear as dark areas on the dorsum in the post-burn $S_tO_2$ images. However, the site of the superficial injury displays a distinctly different response compared to the more severe burn sites. Oxygenation increases at the superficial burn site in comparison to its pre-burn levels. This increase corresponds to the visible erythema or tissue reddening associated with minor burns. Hair also appears dark in the oxygen saturation images but is easily distinguished from areas of tissue with low oxygen saturation.

Depth Spectroscopy

Figure 7:
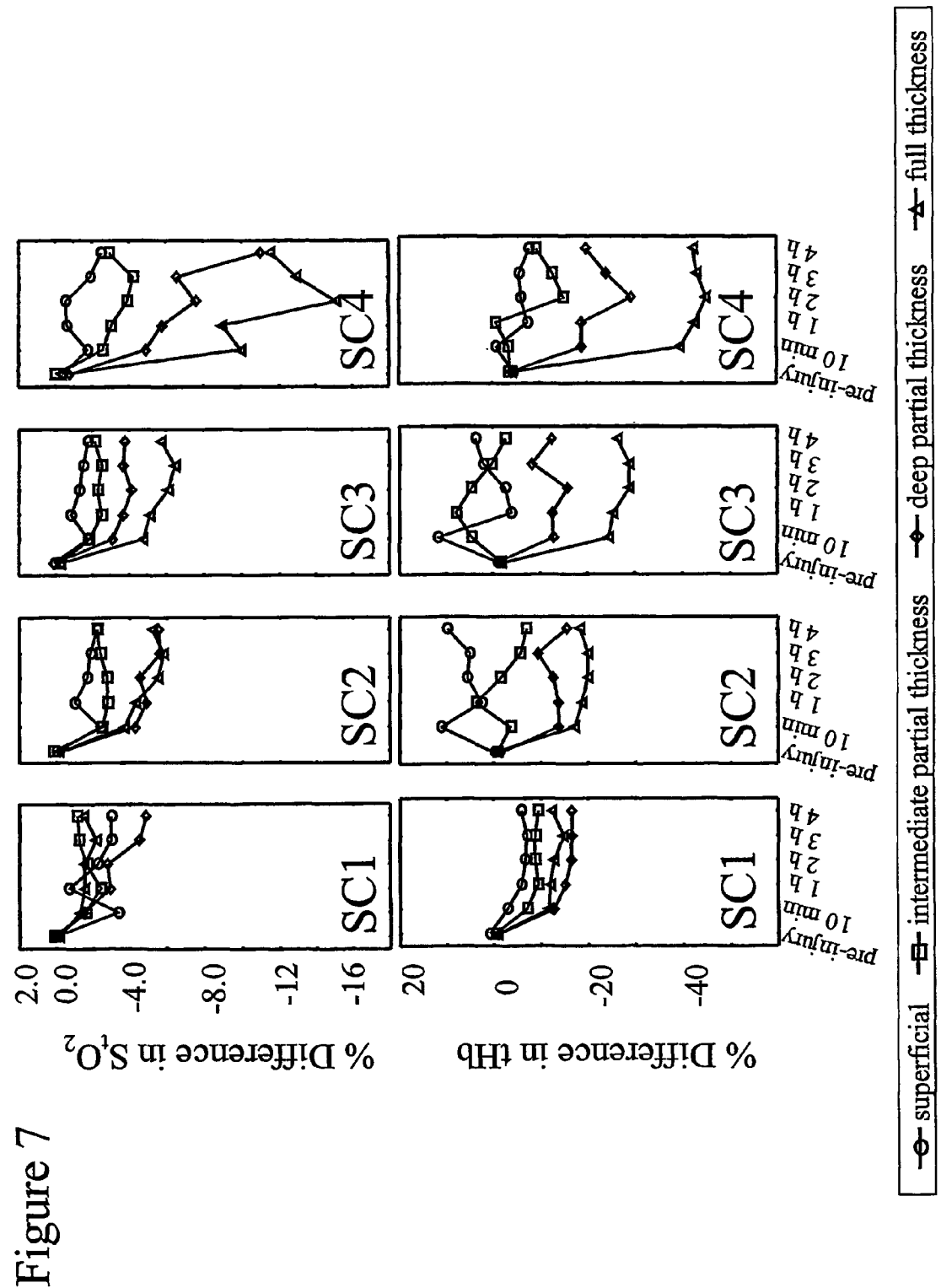
FIG. 7 shows burn hemodynamics as a function of source-collector (SC) separation during the early post-burn period. The top panels denote the oxygen saturation changes and the lower panels the blood volume. The four source-collector separations, denoted SC1 through SC4, correspond to probe separation distances of 1.5, 3, 4.5 and 6 mm.

Regardless of the degree of injury, all burns show an immediate post-injury alteration in the oxygen saturation and blood volume as displayed in FIG. 7. The figure summarizes the hemodynamic for the various burn injuries in relation to the source-collector separation or sampling depth into the tissue. All burns exhibit an instantaneous decrease in the tissue oxygenation following the injury. Results from the smallest source-collector separation show no significant difference in the oxygen saturation between burns of different severity relative to the uninjured control tissue. These results were expected since the smaller source-collector separations probes primarily the epidermis, however, the epidermis is mainly avascular depending on the capillary beds in the dermis for oxygen. Thus, there is little or no hemoglobin contribution to the spectral signature from the smallest source-collector separation. As the source-collector separation increases, the tissue sampling depth is extended from the epidermis to the dermis and the burn injuries commence to become discernible. Despite the ability to distinguish oxygenation at various depths, intermediate and deep partial thickness injuries cannot be reliably isolated on the basis of oxygenation measurements.

Total hemoglobin, displayed in the bottom panels of FIG. 7, provides an efficient indicator of blood volume alterations following a burn injury as a function of probe depth. Again, the burn injuries are indiscernible when probing with the smallest source-collector separation since it is primarily the epidermis that is probed. As the deeper tissue is probed using the larger source-collector separations, the superficial and intermediate partial thickness burns exhibit a notable alteration from the pre-burn state. Superficial injuries show a sudden increase in the [tHb] resulting from the injury illustrating a hypervolemic state followed by a decrease or hypovolemic and finally steady increase over the 4 h. Partial thickness injuries also undergo an increase in [tHb]. However, this increase in [tHb]. peaks later (2 h following the injury) and is longer lived than the superficial response. The blood volume changes in the deep partial and full thickness injuries are remarkably different from that observed in the less severe injuries. The deep partial wound also demonstrates a hypervolemic peak, however hypervolemia occurs towards the end of the study. Small source-collector separation distances probe the topmost layer of the skin, however, this layer has sustained heavy damage with only a limited micro-circulation to supply blood to the injured site. Examining deep wounds at these small source-collector separations, one is primarily sampling heavily wounded tissue. On the other hand, large source-collector separations permit sampling of deep tissue, in particular, the viable tissue underneath the destroyed visible tissue. Therefore, large source-collector separations are ideally suited to distinguish deep partial from full thickness injuries, whereas, small source-collector separations are better suited for distinguishing between superficial and intermediate wounds. Each of the various hemodynamic parameters provides information on the status of the tissue following a thermal insult. Combining several of these parameters along with the added information of sampling depth, one can isolate and grade the burn injury.

Example IV

Results and Discussion

Figure 3:
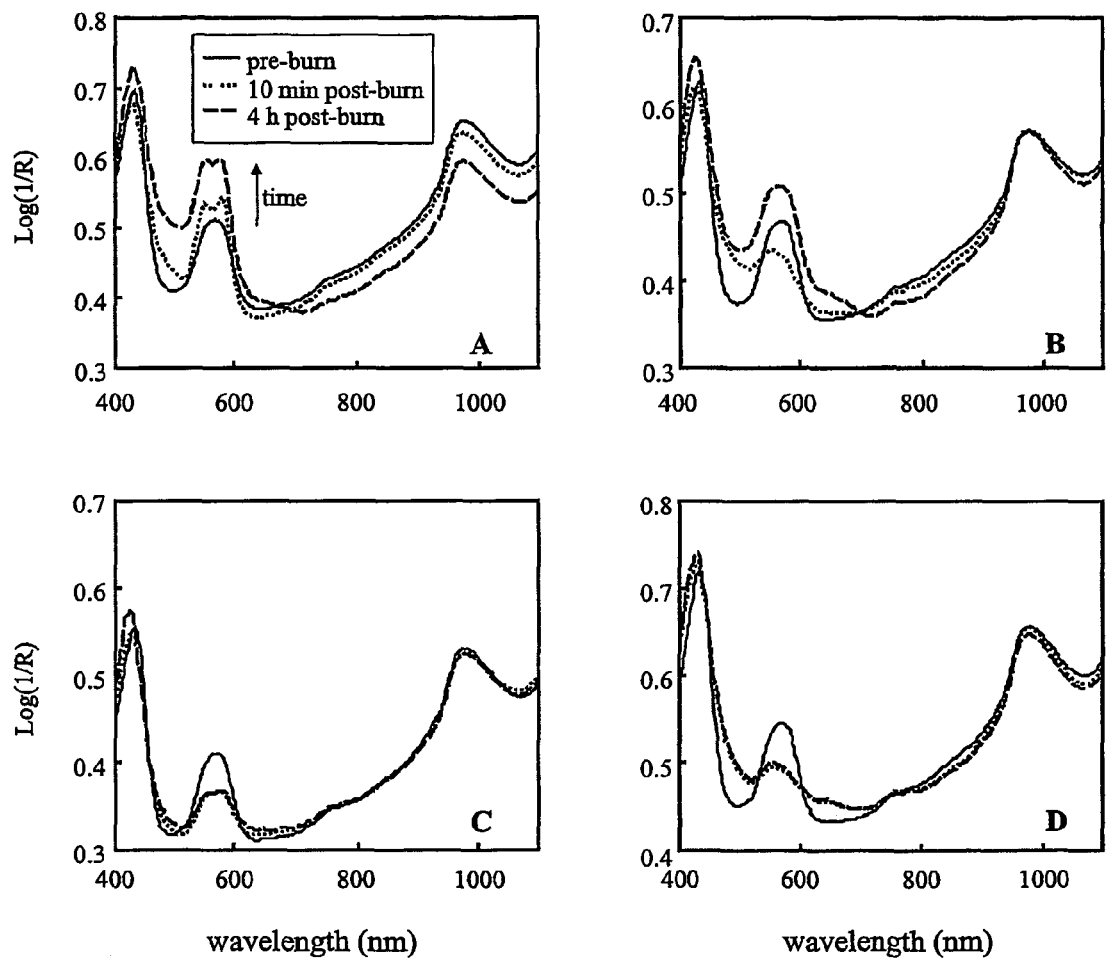
FIG. 3 is a series of spectra in which a multiplicative scatter correction method was applied to the raw visible-near infrared spectra of thermally injured porcine skin. Representative results (n=1) for superficial (A), intermediate (B), deep partial (C), and full thickness (D) burn sites are displayed.

Burn injuries drastically modify both the physical and optical properties of skin. PARAFAC is used to investigate the spectral changes that accompany a thermal injury. Prior to the PARAFAC analysis, a multiplicative scatter correction is applied to the data to compensate for additive and multiplicative differences between spectra taken at different times at the same burn site. Applying a multiplicative scatter correction to the data has the advantage of removing unwanted constants and multiplicative effects in the data. The multiplicative scatter correction also simplifies data comparison by standardizing data across replicated series of measurements. Representative time series of multiplicatively scatter corrected spectra for each type of burn are presented in FIG. 3.

Figure 4:
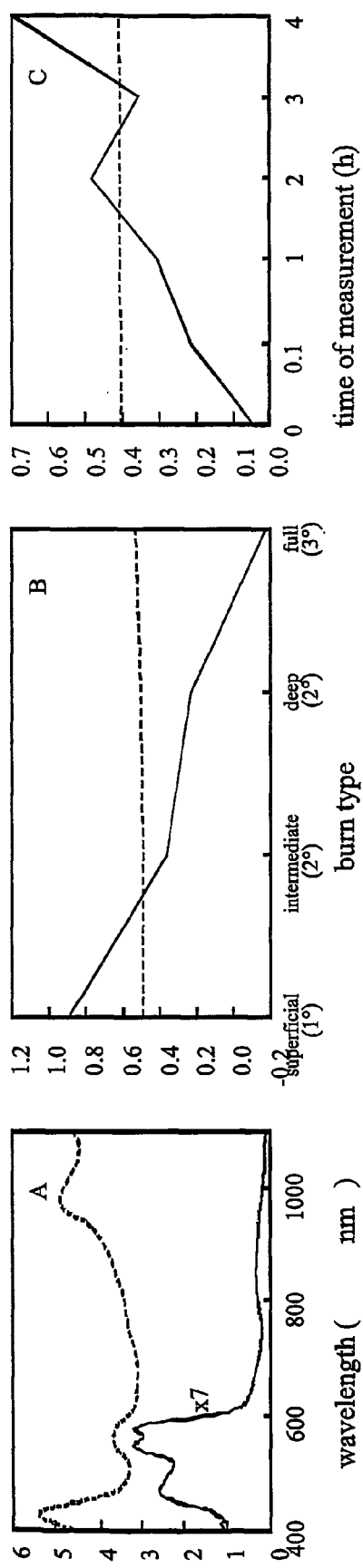
FIG. 4 is a series of spectra of thermally injured porcine skin analyzed using the PARAFAC method. Representative results (n=1) are displayed with respect to wavelength (A), burn type (B), and time (C).

The results from a two-factor three-way PARAFAC analysis of the data for a single animal are summarized by the computed wavelength, thermal insult and time loadings shown in FIG. 4. The loading wavelengths of FIG. 4A reveal the two "pure" spectral components or factors that are retrieved by the analysis. The first wavelength factor (dashed line) has distinctive spectral features at 555 and 760 nm consistent with the spectrum of deoxyhemoglobin as well as an absorption feature at 980 nm which is characteristic of water. Thus the first factor appears to consist of contributions from both deoxyhemoglobin and water. The second factor (solid line) resembles an oxyhemoglobin spectrum with its unique vibronic transition bands at 540 and 580 nm. The broad absorption band between 800 and 1000 nm, which is consistent with the broad near infrared charge transfer band of oxyhemoglobin, is also evident. These results suggest the data can be represented by two distinct spectra (factors), one resembling the combined deoxyhemoglobin and water contribution and the other representing the oxyhemoglobin contribution.

The wavelength loading factors obtained from the PARAFAC analysis suggest that thermal burns alter oxy- and deoxy-hemoglobin concentrations. The thermal insult loading vectors given in FIG. 4B indicate the relative changes in the wavelength factors (components) for the different types of burns. The first thermal insult factor (dashed line) displays only a moderate change between the different burn types with a slight upward trend between the superficial (1°) and full thickness (3°) burns. This suggests the deoxyhemoglobin and water contribution in the spectral response undergoes a minor change with the thermal insult. The second factor in the loading (solid line) shows a steady decline, suggesting that the oxyhemoglobin content of tissue decreases with increasing severity of the burn injury. These results indicate that the severity of a burn injury has a direct effect on the oxy- and deoxy-hemoglobin balance within the injured tissue. The superficial and full thickness burns represent the two extremes in the second thermal insult loading. The intermediate and deep partial thickness burns are similar, differing only in the extent of damage to the dermis. These injuries have intermediate values in the thermal loading vector. More importantly, the loading values scale with the magnitude of the injury.

Figure 5:
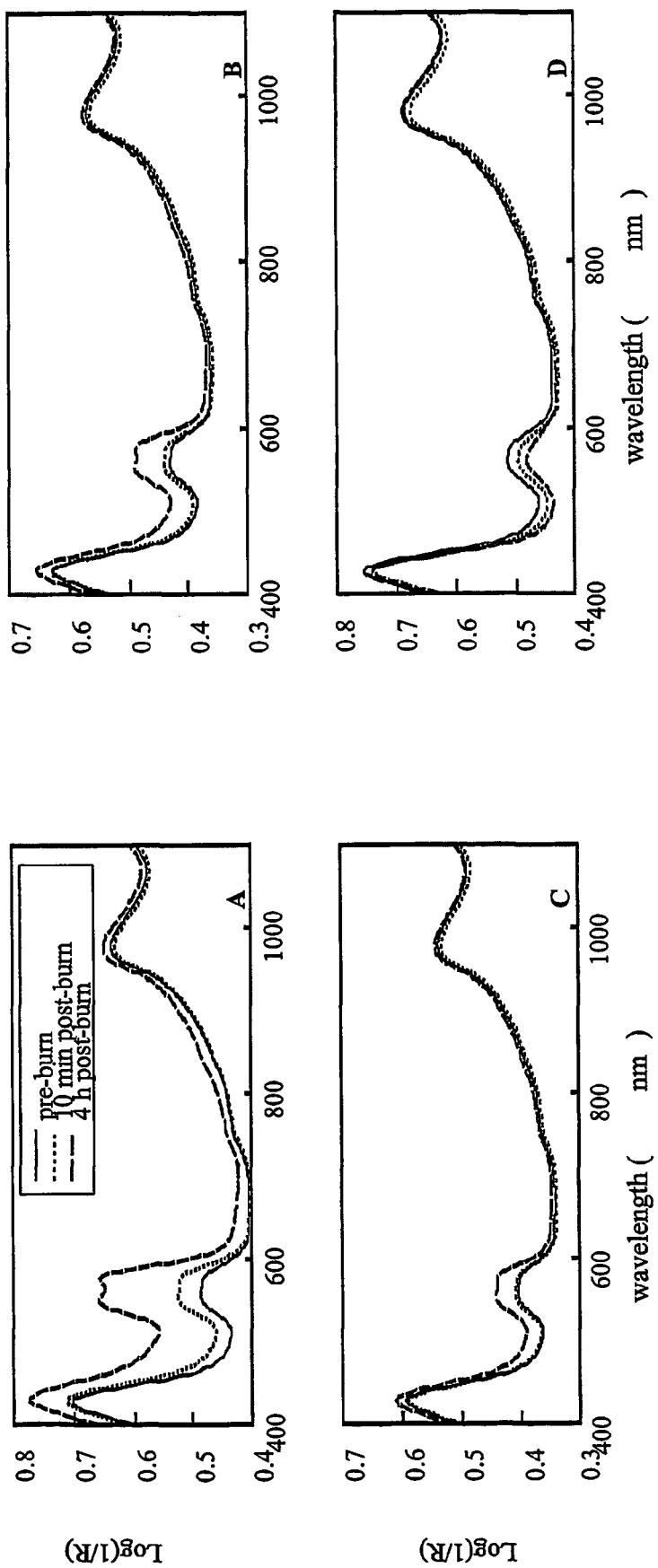
FIG. 5 is a series of spectral data reconstructed using the wavelength, thermal insult, and time loading factors that were determined by the PARAFAC analysis. The reconstructed data for one set of superficial (A), intermediate (B), deep partial (C), and full thickness (D) burns is shown.

Burn injuries are a dynamic process whereby burn depth can become progressively worse during the first few hours following the injury. The time loading factors, FIG. 4C, describe the general trends of the two wavelength factors over the time course of the study. The first time loading factor (dashed line) which is associated with the deoxyhemoglobin content of tissue, exhibits a small but slow increase with time. This indicates that the deoxyhemoglobin-water content of tissue increases slightly and slowly following the burn injury. On the other hand, the second time loading factor (solid line) which corresponds to the oxyhemoglobin content of tissue, displays an enormous change over time. This change is equivalent to a large positive change in the oxygen content of the tissue over time. The thermal insult loadings suggest that thermal injuries have a profound effect on the oxygen balance not only at the onset of the injury but also over time. In order to assess the quality of the two-factor model and more clearly demonstrate the changing oxygen balance between burns of different severity, the data was reconstructed using the factors determined from the PARAFAC analysis. Applying equation 3 to the PARAFAC wavelength, thermal insult, and time loading factors, the data was reconstructed and is displayed in FIG. 5.

The main trend observable with the superficial burn is the large increase in the oxyhemoglobin contribution to the spectrum as demonstrated in FIG. 5A. This increase in oxyhemoglobin, which results from an influx of blood to the injured tissue, becomes apparent immediately following the injury and continues to rise over the 4 h postburn monitoring period. On the other hand, intermediate and deep partial thickness burns (FIGS. 5B and 5C) undergo a greater amount of tissue damage. Although they do show an increase in oxyhemoglobin following the injury, the response is invariably less dramatic. While it only takes 10 minutes for the oxyhemoglobin content of the tissue to increase significantly following a superficial burn, the response of intermediately burned tissue is minimal. Following a deep partial thickness injury, the change in oxyhemoglobin is further reduced, almost nil. The cutaneous blood supply at the dermis and its relation to the extent or depth of tissue damage explains why there are varying degrees of oxyhemoglobin following burn injuries. Increased depth of thermal injury means there is a greater portion of the vessels that are damaged and as a result are no longer capable of transporting oxygenated blood to the tissues. Since deep partial thickness injuries extend further into the dermis than intermediate ones, it is not surprising that less oxygen is available for tissue consumption. The even deeper, full thickness burns obliterate both the epidermis and dermis completely, thereby making the skin avascular. Rather than observing an increase in the oxygen content of the tissue, the full thickness injuries experience a drop in the oxyhemoglobin contribution to the spectra following the insult. This drop becomes evident within 10 minutes of the thermal insult and continues to decrease at the full thickness burn site over the 4 h monitoring period of the study. Since full thickness burns involve total destruction of the vascular supply to cutaneous tissue, skin that has suffered such an insult has no supply of oxygenated blood and will eventually die.

Multi-way parallel factor analysis was used to investigate and compare the spectroscopic time courses of the response of tissue to burn injuries of varying magnitude. The multi-way analysis could be done in an exploratory fashion requiring little or no prior information on the system other than that information required to determine the constraints imposed by the experimental design and the nonnegativity constraint associated with generic spectral response of any component species present in a multi-component system. The two-component three-way analysis extracts two wavelength factors, one resembling the combined deoxyhemoglobin and water contribution and the other representing the oxyhemoglobin contribution to the spectra. These results indicate that the severity of a burn injury has a direct effect on the oxy- and deoxy-hemoglobin balance within the injured tissue. Reduced tissue oxygenation in deep partial thickness and full thickness injuries may ultimately contribute to tissue necrosis following a severe burn injury. Parallel factor analysis reveals that the spectral changes in the early post-burn period can be faithfully represented by two "pure" components that summarize the oxy- and deoxy-hemoglobin balance within the injured tissue. Analysis of the visible-near infrared spectroscopic data indicated that the oxy- and deoxy-hemoglobin balance in injured tissue changed over time following the injury. However, within the early post-burn period the oxy- and deoxy-hemoglobin balance scaled with the degree or depth of thermal injury. Visible-near infrared spectroscopic assessment of the oxy- and deoxy-hemoglobin balance in injured tissue could clearly distinguish superficial and full thickness injuries and may also provide an indicator sensitive enough to distinguish between intermediate and deep partial thickness burns.

In general, the injured sites all show an immediate visual change following the thermal injury as displayed in FIGS. 2b and c. Based on the visual appearance of the wound, the superficial wound is distinct from remaining wounds. However, the partial and full thickness injuries are difficult to identify using visual observation. Physiological monitoring (heart rate and blood pressure) as well as blood samples were taken prior to the burn injury, immediately following the injury and at hourly intervals for the duration of the protocol. Since less than 1% of the total body surface area is injured in this model, no systemic response was expected. Blood gas analysis showed no indication of systemic response to the thermal injury. Blood gases remained within the normal range for all animals for the duration of the protocol. The near infrared spectral data from both the uninjured (control) and injured (burn) sites were processed as described in the methods section to obtain $S_tO_2$ and tHb hemodynamic parameters.

The control sites displayed no significant variation in any of the parameters 4 hrs following the thermal burn insult. These results are consistent with the physiological monitoring and blood gas results that indicate no significant systemic effects on the animal due to the thermal injury. While no systemic response was observed as a result of the burn injury, regionally changes were observed in the areas of tissue subjected to thermal damage.

Oxygen Saturation

Figure 9A:
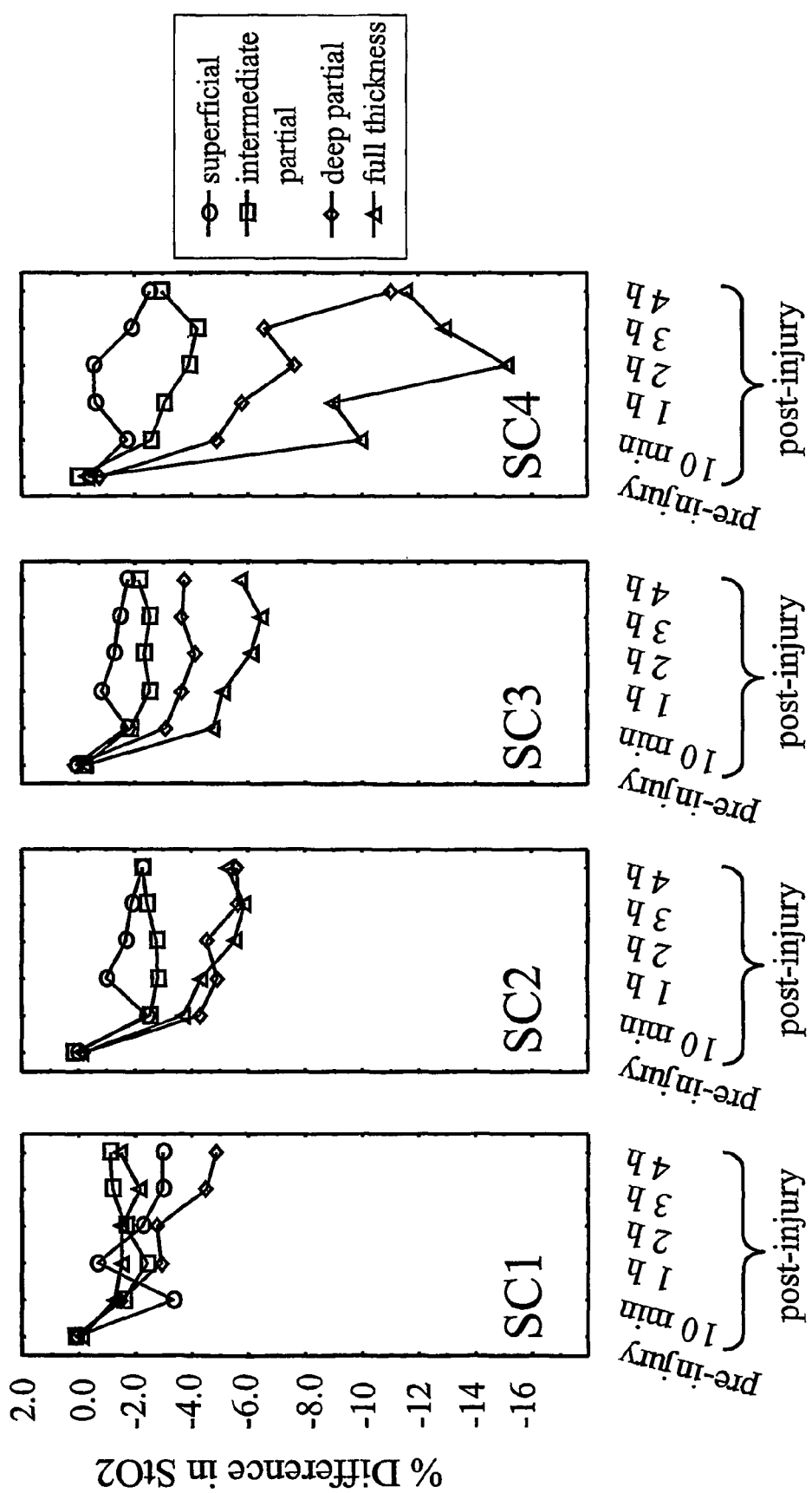
FIG. 9 shows the computed a) $StO_2$ and b) tHb for the superficial, intermediate partial, deep partial and full thickness burns at the various source-detector distances over early post burn period.

FIG. 9a describes the difference in the oxygen saturation for the various burns injuries in relation to the response measured at a nearby control site for the various source-detector separations. All burns show an instantaneous decrease in the oxygenation following a burn injury.

Results from this panel are greatly inconsistent and were expected with regards to tissue oxygenation. This panel contains the $S_tO_2$ for the smallest source-detector separation which was designed to probe the outermost layer of the skin, namely the epidermis. However, the epidermis is mainly an avascular layer of tissue which depends on the capillary beds in the dermis for oxygen. As such, the method is not appropriate to determine the oxygen content in this tissue layer. The superficial injuries show a minor decreasing change $S_tO_2$ with certain level of recovery observed towards the end of the 4 hrs period. Examining the $S_tO_2$ at the various source-detector geometries, one notices changes throughout the different fiber optic separations implying that superficial burns actually extent deep within the tissue as well. However, the magnitude of the changes would suggest that this type of injury is minor, only disrupting the tissue.

The remaining burns are highly destructive, obliterating the epidermis and damaging or destroying the dermis. Regardless of the severity of the injury, all show a distinct drop in the $S_tO_2$ succeeded by a steady decline over the 4 hrs post burn period. As a whole, the superficial and full thickness burns are well distinguishable at any of the source-detector separations. At the appropriate source-detector separation, the intermediate partial thickness burn is also discernible from the deep partial thickness injury. Considering the extent of the damage and the volume probe by the various source-detector separations, partition of the various burns is possible. At the smaller probe separation, it becomes difficult to identify the intermediate partial, deep partial, and full thickness thermal injuries. At smaller source-detector separations, the depth probed into the tissue is not deep enough to distinguish the damage from the viable tissue. As the probe separation is increases, damaged and healthy tissue is probed depending on the depth of the thermal injury, thus permitting the separation of the various burns. Despite this ability to distinguish oxygenation at various depths, intermediate and deep partial thickness injuries cannot be reliably isolated on the basis of $S_tO_2$ measurements made in the early post-burn period of a thermal injury.

Total Hemoglobin

Figure 9B:
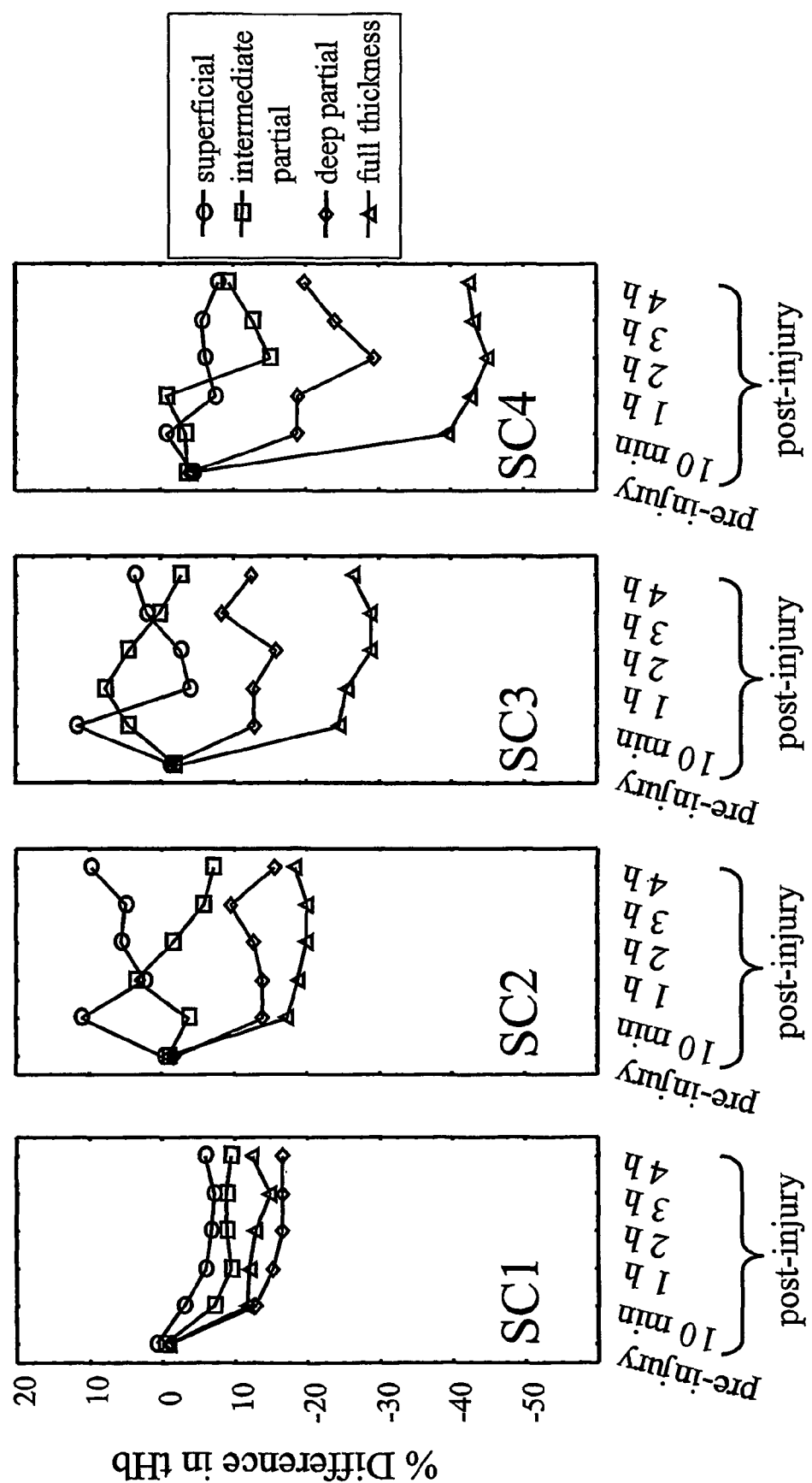

Total hemoglobin, as displayed in FIG. 9b, provided an efficient indicator of blood volume status following a burn injury. Superficial injuries show a sudden increase in the tHb resulting from the injury illustrating a hypervolemic state followed by a decrease or hypovolemic and finally steady increase over the 4 hrs. Superficial burns are considered minor burns, mildly disrupting normal microcirculation in the skin.

Partial thickness injuries also undergo an increase in tHb. However, this increase peaks later (2 hrs following the injury) and is longer lived than the superficial response. At the shortest probe separation, it is difficult to distinguish the various injuries other than the superficial burn. As stated earlier, the epidermis is primarily avascular; however, the influx resulting from the thermal injury does extend to some degree into the dermis. As source-detector separation increases, the injuries become distinguishable, beginning with the superficial with the familiar hyper hypo increase, followed by the intermediate partial thickness burn. Intermediate partial thickness burns impairs the uppermost layer of the dermis, with the remaining basement layer intact. This bottom layer is capable of providing a large inrush of blood to the injured site. In some respects, intermediate partial thickness injuries are not much more than slightly extended superficial burns. These results would suggest tHb with the intermediate partial thickness injury would continue to decrease analogous to the superficial but at a reduced rate to provide the necessary blood to remedy the injury. The deep partial wound also demonstrates a hypervolemic peak, however hypervolemia occurs towards the end of the study. At the shorter source-detector separation, it is difficult to observe the sudden change in tHb associated with thermal injuries. As mentioned earlier, short probe separation distances probe the topmost layer of the skin; however, this layer has sustained heavy damaged with only a limited microcirculation to supply blood to the injured site. At these separations one is moreover sampling heavily wounded tissue. An increased separation permits sampling of the viable tissue underneath the wound and it is this layer which supports and advances healing.

Full thickness injuries, the most destructive of the thermal injuries exhibited large changes over the 4 hrs study period. This is consistent with the premise that full thickness injuries extensively damage the tissue to the extent of destroying the microcirculation to the epidermis and the dermis. The results suggest a very large difference prior and post the injury suggesting the tissue has sustained heavy damage with no possibility of recovery. Each of the various hemodynamic parameters provides information on the status of the tissue following a thermal insult. The combined result of lack of tHb increase and decrease $S_tO_2$ in combination correlates well with the expected outcome, which is that the circulation has been damaged and that whatever blood is present is slowly being dissipated. Eventually, since the vasculature has been destroyed and the site is slowly becoming deoxygenated, this injury will result in necrosis and tissue death.

Individually, categorizing the various thermal injuries based solely on any one parameter is not possible. Each of the various parameters provides information on the status of the tissue following a thermal insult. Oxygen saturation can be used to differentiate a minor injury (superficial burn) from the damaging partial and full thickness injuries. This parameter was also explored against the different source-detector positions. The oxygen saturation results indicate that at the proper probe position, one can distinguish the partial thickness wounds from the other injuries. More importantly, the oxygen saturation of the various partial thickness injuries are discernible from one another. In general, a burn specialist is capable of classifying superficial and full thickness burns using exclusively the visual appearance of the wound. The difficulty lies in distinguishing the various levels of damage caused by partial thickness burns. Of the visually discernible burn injuries, the superficial is the simplest to assess. Burns have a dramatic influence on the relative amount of blood present after a burn injury, especially with the more invasive of the thermal injuries. Total hemoglobin levels reflect tissue blood volume or the extent of blood perfusion. The larger the destruction to the tissue, the lower the blood or available blood present at the injured site. As seen in FIG. 9, the intermediate, deep, and full thickness injuries are definitely differentiated based on tHb changes at the injured site. These results correlate well with what is known about these injuries and the effects they have on the microcirculation. Total destruction of the microcirculation results in no blood available to regenerate the injury as seen with the full thickness injury. Using the combined available information of a decrease in the $S_tO_2$ and lack of an increase of tHb, the predicted outcome of this tissue is necrosis. Separately, each parameter provides a portion of the description of the thermal injury with time. When all the measurements are taken as a whole and examined relative to one another, the superficial, intermediate, deep, and full thickness injuries can be differentiated.

Tissue responds differently depending on the severity of the insult. The results suggest burns can be differentiates based on a time series over the first 4 hrs following the injury. The two extreme cases of a thermal injury, namely the superficial (a mild injury) and full thickness (a severe injury) injuries, were definitely distinguishable. Using the proper probe arrangement, the intermediate partial thickness injury can be isolated from the superficial and deep partial thickness injuries based on oxygen saturation measurements. However, deep partials and full thickness resemble one another with regards to this hemodynamic parameter. The different source-detector separations were unable to separate these injuries as well. Total hemoglobin, a useful parameter, demonstrated a marked difference in response with the partial and full thickness injuries. The combined parameters of oxygen saturation and total hemoglobin provide a more appropriate description of the thermal injury. In particular, using both hemodynamic parameters, one can identify the different burn injuries. This study was designed to investigate thermal injuries immediately following the burn. Water may be usefully parameter a few hours after the initial thermal injury once edema has settled in.

Near infrared spectral measurements in tissue can provide a clinically noninvasive or minimally invasive method to distinguish between thermal injuries of varying severity. Thermal injuries alter the oxygen content and blood perfusion as well as the water content of the tissue. Physiological parameters of oxygen saturation total hemoglobin, and water were determined from a time series of near infrared reflectance spectra. These parameters were used to assess and distinguish different thermal injuries utilizing a porcine burn model.

While the preferred embodiments of the invention have been described above, it will be recognized and understood that various modifications may be made therein, and the appended claims are intended to cover all such modifications which may fall within the spirit and scope of the invention.

The invention claimed is:

1. A method of characterizing a burn comprising:
   emitting a beam of light at a wavelength between 500 to 1100 nm from a source into a burnt tissue portion;
   collecting and analyzing reflected light from the beam with a detector at a first separation distance from the source, thereby producing a first depth spectrum;
   emitting a beam of light at a wavelength between 500 to 1100 nm from a source into a burnt tissue portion;
   collecting and analyzing reflected light from the beam with a detector at a second separation distance from the source, thereby producing a second depth spectrum;
   investigating depth dependent circulatory alterations by comparing oxyhemoglobin and deoxyhemoglobin balance within the burnt tissue portion from the first depth spectrum and the second depth spectrum; and
   categorizing the burn based on said comparison.

2. The method according to claim 1, wherein the first depth spectrum and the second depth spectrum are compared over spectral regions corresponding to at least one of the following: oxygen saturation, total hemoglobin, hydration or oxyhemoglobin levels.

3. A method of characterizing a burn comprising:
   at a first time point:
   (a) emitting a beam of light at a wavelength between 500 to 1100 nm from a source into a burnt tissue portion;
   (b) collecting and analyzing reflected light from the beam with a detector at a first separation distance from the source, thereby producing an early first depth spectrum;
   (c) emitting a beam of light at a wavelength between 500 to 1100 nm from the source into a burnt tissue portion;
   (d) collecting and analyzing reflected light from the beam with a detector at a second separation distance from the source, thereby producing an early second depth spectrum;
   at a second time point:
   (e) emitting a beam of light at a wavelength between 500 to 1100 nm from the source into a burnt tissue portion;
   (f) collecting and analyzing reflected light from the beam with a detector at the first separation distance from the source, thereby producing a late first depth spectrum;
   (g) emitting a beam of light at a wavelength between 500 to 1100 nm from the source into a burnt tissue portion;
   (h) collecting and analyzing reflected light from the beam with a detector at the second separation distance from the source, thereby producing a late second depth spectrum;
   (i) investigating depth dependent circulatory alterations over time by comparing oxyhemoglobin and deoxyhemoglobin balance within the burnt tissue potion from the early first depth spectrum to oxyhemoglobin and deoxyhemoglobin balance from the early second depth spectrum and comparing oxyhemoglobin and deoxyhemoglobin balance within the burnt tissue potion from the late first depth spectrum to oxyhemoglobin and deoxyhemoglobin balance from the late second depth spectrum; and
   (i) determining if burn depth has become worse over time based on said investigation.

4. The method according to claim 3 wherein the first depth spectrum and the second depth spectrum are compared over spectral regions corresponding to at least one of the following: oxygen saturation, total hemoglobin, hydration or oxyhemoglobin levels.

5. The method according to claim 4 wherein superficial burns are characterized by a sudden increase in total hemoglobin, an increase in oxygen saturation and an increase in oxyhemoglobin levels.

6. The method according to claim 4 wherein partial burns are characterized by a decrease in oxygen saturation, a slow increase in total hemoglobin and a slight increase in oxyhemoglobin levels.

7. The method according to claim 4 wherein deep partial burns are characterized by a slow increase in total hemoglobin, no increase in oxyhemoglobin levels and an increase in hydration.

8. The method according to claim 4 wherein full thickness burns are characterized by no change in total hemoglobin, a decrease in oxyhemoglobin levels and no change in hydration.

* * * * *